United States Patent
Erickson et al.

(10) Patent No.: US 6,352,714 B1
(45) Date of Patent: Mar. 5, 2002

(54) METHOD OF PRODUCING A METAL NUTRIENT FOR AN ANIMAL FEED

(75) Inventors: Paul R. Erickson, Glendale; Lloyd J. Uhren, Waukesha, both of WI (US)

(73) Assignee: DER, Inc., Elkhorn, WI (US)

( * ) Notice: Subject to any disclaimer, the term of this patent is extended or adjusted under 35 U.S.C. 154(b) by 0 days.

(21) Appl. No.: 09/614,037

(22) Filed: Jul. 11, 2000

(51) Int. Cl.$^7$ .................. A23K 1/165; A61K 35/12; A61K 33/24
(52) U.S. Cl. ................ 424/442; 424/572; 424/655; 530/343; 530/400; 514/2
(58) Field of Search ................. 424/442, 295, 424/572, 655; 423/179.5; 252/546; 528/38; 210/759; 260/123.7; 530/343, 400; 514/2

(56) References Cited

U.S. PATENT DOCUMENTS

| | | | |
|---|---|---|---|
| 3,941,818 A | | 3/1976 | Abdel-Monem |
| 3,950,372 A | | 4/1976 | Abdel-Monem |
| 3,969,540 A | | 7/1976 | Jensen |
| 4,021,569 A | | 5/1977 | Abdel-Monem |
| 4,067,994 A | | 1/1978 | Anderson et al. |
| 4,100,154 A | * | 7/1978 | Holloway et al. ........ 260/123.7 |
| 4,167,564 A | | 9/1979 | Jensen |
| 4,183,947 A | * | 1/1980 | Cockerill et al. ............ 424/295 |
| 4,207,297 A | * | 6/1980 | Brown et al. ............ 423/179.5 |
| 4,619,984 A | * | 10/1986 | Yuki et al. .................... 528/38 |
| 4,863,898 A | | 9/1989 | Ashmead et al. |
| 5,087,623 A | | 2/1992 | Boynton et al. |
| 5,087,624 A | | 2/1992 | Boynton et al. |
| RE33,988 E | | 7/1992 | Evans |
| 5,175,156 A | | 12/1992 | Boynton et al. |
| 5,278,329 A | | 1/1994 | Anderson |
| 5,470,510 A | * | 11/1995 | Willey et al. ................ 252/546 |
| 5,591,878 A | | 1/1997 | Nelson et al. |
| 5,707,679 A | | 1/1998 | Nelson |
| 5,905,075 A | | 5/1999 | Harpe et al. |
| 5,908,560 A | * | 6/1999 | Elliott et al. ................. 210/759 |
| 5,929,066 A | | 7/1999 | McCarty |
| 5,948,772 A | | 9/1999 | de la Harpe et al. |

FOREIGN PATENT DOCUMENTS

DE        1984-171985      *   7/1984

* cited by examiner

Primary Examiner—Christopher R. Tate
Assistant Examiner—Randall Winston
(74) Attorney, Agent, or Firm—Andrus, Sceales, Starke & Sawall, LLP

(57) ABSTRACT

A leather hydrolysate metal proteinate to be used as a metal nutrient for an animal feed. Chrome tanned leather scrap and shavings are heated in an aqueous solution with an alkali material to produce a water soluble, low molecular weight protein hydrolysate and insoluble chromium compounds which are subsequently separated from the hydrolysate. The hydrolysate is then oxidized to remove any objectionable trace organic residuals from the tanning process, and a di- or tri-valent water soluble metal salt is mixed with the hydrolysate to provide a metal proteinate. The metal proteinate, either as a liquid or a dried powder, can be used as animal or aquaculture diets.

5 Claims, No Drawings

METHOD OF PRODUCING A METAL NUTRIENT FOR AN ANIMAL FEED

BACKGROUND OF THE INVENTION

It has been recognized that trace elements, such as chromium, iron, zinc, copper, phosphorous, manganese and magnesium, have benefit as a dietary supplement for animal and poultry feeds. For example, trivalent chromium is a known cofactor with insulin; together they metabolize carbohydrates and glucose particularly during stress, such as heat, birth or transport, and during the early growth phases. Adequate dietary intake of zinc in animal and poultry is recognized as preventing skin conditions and providing healthy growth and increased weight. It is also recognized that iron is essential to the elementary metabolic process in the cell in preventing iron-deficiency anemia.

If the trace metals are merely added to the animal feed as an inorganic salt, a substantial portion of the metal is passed through the animal with the manure and urine and the nutrient deficiency problems remain unsolved. With large animal feed lots, the disposal of manure containing large amounts of trace elements can be a severe environmental problem.

In order to increase the biological availability of trace metals, it has been proposed to utilize the metals as amino acid metal proteinates or complexes. Not only does the proteinate render the metal more available to the biochemical system of the animal, but also reduces the amount of metal that is passed through the animal as manure. For example, U.S. Pat. No. 5,278,329 is directed to a metal complex of methionine to be used as an animal feed, while U.S. Pat. No. 5,948,772 is directed to a dietary feed supplement consisting of chromium tripicolinate. Not previously realized, however, is the extent to which leather scrap can be used to prepare such proteinates or complexes. In fact, prior efforts have been directed to the removal of complexed metals.

Chromium leather waste consists of chromium-tanned, unfinished leather shavings, trimmings and/or fleshings. In the past, the chrome leather waste was merely discarded to a landfill, but U.S. Pat. No. 4,100,154 describes a method of converting chrome leather waste into a protein hydrolysate and for recovering chromium compounds from the waste. In accordance with the aforementioned patent, the leather waste is heated in an aqueous solution of an alkali material, such as calcium oxide or calcium hydroxide, for a period of time to sever the chromium linkages and dechrome the leather. Through this process, the original collagen of the leather is reduced to low molecular weights, thereby producing a water soluble protein hydrolysate and water insoluble chromium compounds. According to U.S. Pat. No. 4,100,154, the precipitated chromium compounds are separated from the protein hydrolysate and the hydrolysate can then be neutralized with acid to provide an animal feed supplement, while the chromium compounds are washed to remove residual protein and then dissolved in sulfuric acid to provide a water soluble chromium salt useful in tannery operations.

SUMMARY OF THE INVENTION

The invention is directed to a water soluble leather hydrolysate metal proteinate to be used as a feed nutrient and to a method of producing the metal proteinate. In accordance with the invention, chrome-tanned leather scrap and shavings are heated to a temperature generally in the range of 180° F. to 200° F. in an aqueous medium containing an alkali material to hydrolyze the leather scrap and produce a protein hydrolysate along with insoluble chromium compounds. The hydrolyzation reduces the chromium content of the hydrolysate to a value less than 10 ppm of chromium, and the hydrolysate includes a mixture of amino acids with hydroxyproline, aspartic, glycine, proline, glutamic and alanine being the most prevalent acids.

The insoluble chromium compounds are separated by filtration from the hydrolysate. The hydrolysate is carbonated for calcium removal and is then concentrated by evaporation to an approximate 50% solid solution. Following this, an oxidizing material, such as hydrogen peroxide, is added to the hydrolysate to oxidize and eliminate any undesirable trace organics that may remain from the leather tanning operation. After oxidation, a water soluble salt of a di- or tri-valent metal, such as trivalent chromium, iron, manganese, copper, zinc or magnesium is added to the hydrolysate and mixed therewith, preferably by a high shear mixer, to provide a metal hydrolysate proteinate. It is believed that aspartic acid and glutamic acid are the primary agents in chelating, as they have two available sites that accept divalent metals, such as zinc, iron, and the like.

The leather hydrolysate metal proteinate has particular use as a nutrient for animals, poultry and for aquaculture, and provides precise pre-selected control over the assimilation of the metal into the biological system of the animal.

As the metal is present as a hydrolysate proteinate, the bio-availability of the metal is increased and the output of the metal in manure or waste products is reduced thereby decreasing the environmental problem of waste disposal.

Various other features, objects and advantages of the invention will be made apparent from the following description.

DESCRIPTION OF THE PREFERRED EMBODIMENT

In carrying out the invention, chrome leather waste is hydrolyzed using a process such as that disclosed in U.S. Pat. No. 4,100,154. Chrome leather waste can consist of pieces that are trimmed from chrome tanned hides, or fragmented when chrome tanned hide is split into one or more layers, or can consist of shavings, dust or fiber bundles produced when the chrome tanned leather is machine shaved to predetermined thickness. In general, unfinished chrome leather waste contains approximately 3% to 4% trivalent chromium, 12% to 15% other inorganic salts, 3% to 5% fats, oils, and the like and 75% to 80% of protein collagen.

The hydrolysis of the chrome leather waste can be carried out by the external application of heat, or direct injection of steam, to a mixture of the leather scrap, an alkaline material and water, at a starting pH of 10 to 11. The alkaline material is preferably an oxide or hydroxide of calcium or magnesium. Potassium or sodium hydroxide can also be used. The alkaline materials act to hydrolyze the leather scrap and precipitate insoluble chromium compounds in a form that can be readily separated by settling and filtration. More specifically, the mixture is heated to a temperature generally in the range of 180° F. to 200° F., and the heating is continued until the pH of the mixture has decreased to a value in the range of about 8.5 to 9.0. At this stage, the protein is substantially hydrolyzed and the average molecular weight of the collagen has been reduced to a value of about 5,000 to 100,000, with the average molecular weight being from 35,000 to 50,000. The chromium in the chrome leather waste precipitates as insoluble chromium compounds which can be separated from the hydrolysate by filtration or centrifugation.

The resulting protein hydrolysate is water soluble and contains less than 10 ppm of chromium. At this stage, the hydrolysate generally has a concentration of about 10% to 15% solids. The hydrolysate may then be carbonated to remove calcium compounds and is the concentrated, preferably by evaporation, to a solids content of approximately 50%. An oxidizing material, such as a 30% solution of hydrogen peroxide, is added to the hydrolysate in a ratio of about 1:50 to oxidize and remove any potentially undesirable trace organic materials, such as anti-mold chemicals, that were used in the leather tanning process and may remain in the hydrolysate.

The hydrolysate contains a mixture of a number of amino acids and a typical analysis of a hydrolysate is as follows in weight percent:

| Hydroxyproline | 10.52 | Proline | 12.39 |
|---|---|---|---|
| Aspartic Acid | 5.25 | Threonine | 1.30 |
| Serine | 2.22 | Glutamic Acid | 9.33 |
| Glycine | 20.54 | Alanine | 8.63 |
| Cysteine | 0.07 | Valine | 2.10 |
| Methionine | 0.64 | Isoleucine | 1.30 |
| Leucine | 2.81 | Tyrosine | 0.24 |
| Phenylalanine | 1.83 | Hydroxylysine | 1.03 |
| Histidine | 0.59 | Ornithine | 0.46 |
| Lysine | 3.17 | Arginine | 6.88 |
| Tryptophane | <0.04 | Taurine | 0.00 |

Total Amino Acids, % as is powder 91.30

The oxidized hydrolysate, which normally contains approximately 25 ppm of chromium and has a pH in the range of 8.5 to 9.0, is then chelated or bonded with a water soluble divalent or trivalent metal salt to provide a metal hydrolysate proteinate. In this procedure, the metal salt is added, either as an aqueous solution or as a dry powder, to the liquid hydrolysate and mixed therewith, preferably by a high shear agitator, at ambient temperature to produce the proteinate. The metal salt is preferably a sulfate or chloride of a metal, such as zinc, copper, manganese, iron, magnesium, or a soluble mixture of sodium and trivalent chromium sulfate.

While not intended to be limited by theory, it is believed that the glutamic acid and aspartic acid are particularly active in chelating with the metal salt, due to the fact that these acids have two available sites which readily accept divalent metals. With trivalent metals, such as chromium, a combination of molecules is required to obtain the three sites for chelating.

As seen from the above analysis, the hydrolysate contains a substantial population of monoprotic amino acids, glycine, proline and hydroxyproline, totaling 43.45%, each having a single negative charge side that is available for bonding. Thus, it is expected that the hydrolysate can bind into solution high concentration of metals, or combination of metals, with the metal concentration being generally in the range of 10% to 15% by weight of total solids.

Conventional chemistry would predict that metals added to the leather hydrolysate at the alkaline pH of 8.5 to 10 would immediate precipitate as the hydroxide. However, the chelating and/or bonding forces of the amino acids present in the hydrolysate are surprisingly strong and thus the metal proteinates are formed, rather than insoluble hydroxides. This action occurs even though the blending of the metal salts and the amino acids occur at the isoelectric point for most of the nutrient metals.

The metal hydrolysate proteinate can either be added to animal or poultry feed as a liquid, or it can be dried, as by spray drying and added to the feed as a powder. The amount of the proteinate to be added can vary widely, depending upon the nature and size of the animal, and the extent of the animal's nutrient needs and/or deficiency, as well as the desires of the animal owner or nutritionist.

A study was made to determine the effects of chromium leather hydrolysate supplementation in nursery pigs, as compared with other complexes, namely chromium picolinate and a yeast chromium complex. In this study, three groups of forty pigs each, with a mean weaning age of 17.6 days, were fed diets containing the chromium leather hydrolysate proteinate, chromium tripicolinate, or yeast chromium complex. In addition, a control group of forty pigs were not fed a supplement. In all cases, the chromium containing complex contained 400 ppb of chromium. Data relating to the average daily gains were obtained over three phases with Phase I being 0–7 days, Phase II being 8–14 days, and Phase III being 15–21 days.

|  | ADG | ADFI | Gain/Feed |
|---|---|---|---|
| Phase I |  |  |  |
| Chromium Leather Hydrolysate Proteinate | 460 gms | 695 gms | 0.68 |
| Chromium picolinate | 250 | 545 | 0.54 |
| Chromium yeast complex | 270 | 455 | 0.59 |
| Control | 220 | 485 | 0.46 |
| Phase II |  |  |  |
| Chromium Leather Hydrolysate Proteinate | 1.15 kg | 1.64 kg | 0.71 |
| Chromium picolinate | 0.92 | 1.43 | 0.67 |
| Chromium yeast complex | 0.95 | 1.40 | 0.69 |
| Control | 1.07 | 1.49 | 0.71 |
| Phase III |  |  |  |
| Chromium Leather Hydrolysate Proteinate | 1.32 kg | 2.36 | 0.56 |
| Chromium picolinate | 1.26 | 2.61 | 0.48 |
| Chromium yeast complex | 1.32 | 2.15 | 0.61 |
| Control | 1.42 | 2.23 | 0.66 |

In the above Table, ADG is "average daily gain" and ADFI is "average daily feed intake".

The results of the above tests show the chromium leather hydrolysate proteinate provided a significant greater average daily gain (ADG) over the control than the other chromium treatments during Phase I. In Phase II, the leather hydrolysate proteinate also provided a favorable gain, while the other chromium treatments inhibited growth response. Phase III results were similar for all treatments.

These results demonstrate that a metal leather hydrolysate proteinate, prepared according to the method of the present invention, provides significant improvement in early-phase feed efficiency when compared to existing metal complex feed supplements. As the metal is available as a proteinate, it can be readily assimilated in the biological system of the animal. Moreover, the above method permits precise control over the quantity of bioavailable metal nutrient. Together these factors help reduce the output of the metal in the animal waste products, thus reducing the environmental problem of waste disposal containing heavy metals.

Various alternatives and embodiments are contemplated as being within the scope of the following claims particularly pointing out and distinctly claiming the subject matter regarded as the invention.

We claim:

1. A method of producing a metal nutrient for use as an animal feed supplement, comprising the steps of heating a mixture of chrome leather scrap, water and an alkaline material at an elevated temperature in a range of about 180° F. to about 200° F. for a period of time sufficient to produce a protein hydrolysate and insoluble chromium compounds and until the pH of the mixture is reduced to a value of 8.5 to 9.0, separating the hydrolysate from said insoluble chromium compounds at said elevated temperature, adding an oxidizing agent to said hydrolysate to remove any undesirable trace organic materials, and admixing a water soluble metal salt selected from the group consisting of di-valent and tri-valent metals with the hydrolysate to produce a amino acid metal proteinate.

2. The method of claim 1, and thereafter drying the hydrolysate containing said amino acid metal proteinate to produce a powder.

3. The method of claim 1, wherein said metal is selected from the group consisting of zinc, copper, manganese, iron, magnesium, trivalent chromium and phosphorous.

4. A method of producing a metal nutrient for use as an animal or poultry feed, comprising the steps of heating chrome leather scrap in water with an alkali material to an elevated temperature in a range of about 180° F. to about 200° F. for a period of time sufficient to produce a liquid protein hydrolysate containing a plurality of amino acids including glutamic and aspartic acid and also containing insoluble chromium compounds and until the pH of the mixture is reduced to a value of 8.5 to 9.0, separating the protein hydrolysate from said chromium compounds at said elevated temperature, chelating a divalent water soluble metal salt with said glutamic acid and said aspartic acid, to produce amino acid metal proteinates, and thereafter utilizing said hydrolysate containing said proteinates as an animal feed nutrient.

5. A method of producing a metal nutrient for use as an animal or poultry feed, comprising the steps of heating chrome leather scrap in water with an alkali material to an elevated temperature in a range of about 180° F. to about 200° F. for a period of time sufficient to produce a liquid protein hydrolysate containing a plurality of amino acids including glycine, proline and hydroxyproline and also containing insoluble chromium compounds and until the pH of the mixture is reduced to a value of 8.5 to 9.0, separating the protein hydrolysate from said insoluble chromium compounds at said elevated temperature, bonding a water soluble metal salt with said glycine and said proline and said hydroxyproline to produce amino acid metal proteinates, and thereafter utilizing said hydrolysate containing said proteinates as an animal feed nutrient.

* * * * *